(12) United States Patent
Olivier

(10) Patent No.: US 10,835,158 B2
(45) Date of Patent: Nov. 17, 2020

(54) SYSTEM AND METHOD FOR BIOMETRIC IDENTIFICATION USING SLEEP PHYSIOLOGY

(71) Applicant: LifeQ Global Limited, Dublin (IE)

(72) Inventor: Laurence Richard Olivier, Alpharetta, GA (US)

(73) Assignee: LifeQ Global Limited, Dublin (IE)

( * ) Notice: Subject to any disclaimer, the term of this patent is extended or adjusted under 35 U.S.C. 154(b) by 120 days.

(21) Appl. No.: 15/821,206

(22) Filed: Nov. 22, 2017

(65) Prior Publication Data

US 2018/0140228 A1 May 24, 2018

Related U.S. Application Data

(60) Provisional application No. 62/425,977, filed on Nov. 23, 2016.

(51) Int. Cl.
*A61B 5/117* (2016.01)
*A61B 5/00* (2006.01)
(Continued)

(52) U.S. Cl.
CPC ............ *A61B 5/117* (2013.01); *A61B 5/0022* (2013.01); *A61B 5/0031* (2013.01); *A61B 5/0205* (2013.01); *A61B 5/029* (2013.01); *A61B 5/02028* (2013.01); *A61B 5/4812* (2013.01); *A61B 5/4857* (2013.01); *G06K 9/00536* (2013.01); *G16H 10/60* (2018.01); *G16H 10/65* (2018.01); *G16H 40/67* (2018.01); *A61B 5/021* (2013.01); *A61B 5/02405* (2013.01);
(Continued)

(58) Field of Classification Search
CPC ... A61B 5/0002; A61B 5/0024; A61B 5/0205; A61B 5/117; A61B 5/4812; A61B 5/4857; A61B 5/1118; G16H 40/67
USPC ........................................................ 600/301
See application file for complete search history.

(56) References Cited

U.S. PATENT DOCUMENTS 5,719,950 A * 2/1998 Osten ................... A61B 5/1171
382/115
8,679,012 B1 * 3/2014 Kayyali ............... A61B 5/0002
600/301
(Continued)

FOREIGN PATENT DOCUMENTS

WO WO2013148753 10/2013

OTHER PUBLICATIONS

International Search Report/Written Opinion issued by the U.S. Receiving Office dated Feb. 5, 2018; 10 pages.
(Continued)

*Primary Examiner* — Christopher A Flory
(74) *Attorney, Agent, or Firm* — Smith Gambrell & Russell LLP

(57) ABSTRACT

The claimed invention comprises software methods for user continuity and physiological state change assessments through generating biometric profiles of individuals and/or groups of individuals by using physiological input together with biomathematical modeling and machine learning techniques. Intra-individual variation in physiological variables including, but not limited to: heart rate, heart rate variability, pulse waveform and its derivatives, blood pressure, breathing rate, cardiopulmonary coupling, actigraphy and circadian rhythms characteristics, are exploited.

29 Claims, 2 Drawing Sheets

(51) Int. Cl.
*A61B 5/02* (2006.01)
*A61B 5/029* (2006.01)
*G16H 40/67* (2018.01)
*G16H 10/60* (2018.01)
*A61B 5/0205* (2006.01)
*G16H 10/65* (2018.01)
*G06K 9/00* (2006.01)
*A61B 5/021* (2006.01)
*A61B 5/024* (2006.01)
*A61B 5/08* (2006.01)
*A61B 5/11* (2006.01)
*G06N 20/00* (2019.01)

(52) U.S. Cl.
CPC ............ *A61B 5/0816* (2013.01); *A61B 5/112* (2013.01); *A61B 5/1118* (2013.01); *A61B 2562/0219* (2013.01); *G06K 9/00892* (2013.01); *G06K 2009/00939* (2013.01); *G06N 20/00* (2019.01)

(56) References Cited

U.S. PATENT DOCUMENTS

| | | | |
|---|---|---|---|
| 2003/0135097 A1 | 7/2003 | Wiederhold | |
| 2005/0046584 A1* | 3/2005 | Breed | B60C 11/24 340/13.31 |
| 2006/0208169 A1* | 9/2006 | Breed | B60N 2/002 250/221 |
| 2006/0253010 A1* | 11/2006 | Brady | A61B 5/14552 600/324 |
| 2010/0189313 A1* | 7/2010 | Prokoski | A61B 5/7264 382/118 |
| 2010/0191541 A1* | 7/2010 | Prokoski | G06F 19/321 705/2 |
| 2012/0068820 A1 | 3/2012 | Mollicone | |
| 2013/0133055 A1* | 5/2013 | Ali | H04L 63/107 726/7 |
| 2014/0012558 A1* | 1/2014 | Mansi | G16B 5/00 703/11 |
| 2014/0089243 A1* | 3/2014 | Oppenheimer | G06F 21/50 706/46 |
| 2014/0089673 A1 | 3/2014 | Luna | |
| 2014/0128691 A1* | 5/2014 | Olivier | A61B 5/0833 600/301 |
| 2015/0135310 A1* | 5/2015 | Lee | G06F 21/35 726/20 |
| 2016/0085999 A1* | 3/2016 | Oppenheimer | G06F 21/50 726/35 |
| 2016/0110975 A1* | 4/2016 | Oppenheimer | G06F 21/50 340/572.1 |
| 2017/0065230 A1* | 3/2017 | Sinha | A61B 5/7275 |
| 2017/0119318 A1* | 5/2017 | Shay | A61B 5/05 |
| 2017/0143267 A1* | 5/2017 | Kovacs | A61B 5/6887 |
| 2017/0143268 A1* | 5/2017 | Kovacs | A61B 5/6887 |
| 2017/0146385 A1* | 5/2017 | Kovacs | G01G 19/50 |
| 2017/0146387 A1* | 5/2017 | Wiard | G01G 19/50 |
| 2017/0146389 A1* | 5/2017 | Kovacs | G01G 19/50 |
| 2017/0148240 A1* | 5/2017 | Kovacs | G01G 23/36 |
| 2017/0173262 A1* | 6/2017 | Veltz | A61M 5/1723 |
| 2017/0209055 A1* | 7/2017 | Pantelopoulos | A61B 5/02108 |
| 2017/0245769 A1* | 8/2017 | Niehaus | A61B 5/681 |
| 2017/0293356 A1* | 10/2017 | Khaderi | A63F 13/212 |
| 2019/0046099 A1* | 2/2019 | Lee | A61B 5/0261 |

OTHER PUBLICATIONS

Supplementary European Search Report issued by the European Patent Office dated Jul. 2, 2020; 9 pages.

* cited by examiner

Distribution of Heart Rate During Sleep

201 Subject 1

201a Dataset 1

201b Dataset 2

202 Subject 2

202a Dataset 1

202b Dataset 2

SYSTEM AND METHOD FOR BIOMETRIC IDENTIFICATION USING SLEEP PHYSIOLOGY

CROSS-REFERENCE TO RELATED APPLICATIONS

The present invention claims priority to Provisional Patent Application No. 62/425,977, files on Nov. 23, 2016, which is relied upon and incorporated here in its entirety by reference.

FIELD OF INVENTION

The present invention relates to the field of biometric modalities and technologies, physiological signal processing and computation of biological data.

BACKGROUND OF INVENTION

According to the World Health Organization, health care is one of the leading cost categories within the US economy alone. Regardless of the intensity of spending in this sector, when comparing monetary investment to tangible health outcomes, the US is ranked last in the quality of care provided. Moreover, health care and insurance fraud, i.e. the intentional presenting of false information on healthcare claims for the purpose of personal gain by the beneficiary, is associated with estimated losses standing in the billions of dollars annually, with the absorption of the greater part of these costs befalling tax payers.

Concurrent with recent advances in the collection of physiological data and the application thereof, major advances in the operating of wearable devices have empowered users to not only have a better understanding of their personal health and the requirements for a healthy disposition, but also to manipulate the conditions of data collection for personal gain. For example, users can switch devices between each other to be beneficiaries of medical schemes offering rewards for reaching predetermined fitness and dietary goals.

A strong need exists for a simple solution to authenticate patient identity in order to prevent health care and insurance fraud, while strengthening security and privacy as well as convenience, and diminishing costs for beneficiaries, medical facilities and insurance companies alike.

Biometric identification systems that are currently employed in the health care and insurance sectors are cumbersome, time consuming and expensive, and require access to fingerprints, hand veins and face of an individual in order to create a unique signature.

Recent advances in technologies enabling physiological data harvesting, as well as how the resultant data is used and/or applied, has enabled researchers to simultaneously accrue multiple data metrics for an individual, including, but not limited to, fitness metrics, sleep patterns, heart rate, and heart rate variability during events such as, but not limited to, sleep, exercise and rest.

The inventors recognized that existing biometric technologies used for biometric identification are prohibitively expensive, time consuming, invasive and can be, with some innovation from the user, bypassed. Therefore, there is a need for systems and methods used for monitoring physiological state change and assessing biometric user continuity that accurately and reliably monitor and/or identify a user in an unobtrusive and convenient manner.

SUMMARY OF INVENTION

The claimed invention is comprised of software systems and methods that use physiological input acquired during sleep, rest and free-living stages to generate biometric profiles of individuals and/or groups of individuals. These systems and methods can acquire such input through the use of wearable devices. In such aspects, the profiles are directed to a set of parameters that describes the state and variation of a user's physiology during sleep, rest, and free-living stages. For example, the profiles can include a user's heart rate and typical high frequency/low frequency HRV ratio and standard deviation means and standard deviations respectively.

During sleep—a natural, periodically recurring state of immobility during which the nervous system is largely inactive, the eyes are closed, and postural muscles are relaxed—physiology is largely unaffected by conscious behaviour or environmental stimuli. This divide broadens the extent to which cardiopulmonary physiology can be deciphered, as the different sleep stages (for example, REM, stage 1 NREM, stage 2 NREM and stage 3 NREM) also represent different physiological states that manifest in cardiac and pulmonary activity. This activity, and resulting patterns of the vital signs, are generated by a highly similar physiology, unique to an individual, and yet highly varied between individuals. These patterns may be monitored with the use of non-intrusive wearable devices while the subject is asleep in its own surroundings.

In addition to physiological input acquired from wearable devices, input may also be acquired from, for example, but not limited to, medical devices and databases. The intra-individual variation manifesting from physiological metrics acquired during sleep, rest and free-living stages, is exploited to generate said biometric profiles. The physiological metrics can include, but is not limited to, heart rate, heart rate variability, blood pressure, breathing rate, cardiopulmonary coupling, actigraphy, accelerometry, circadian rhythms characteristics, and pulse waveform, its derivatives, and associated pulse shape characteristics, such as augmentation index, left ventricular ejection time (LVET), photoplethysmographic (PPG) rising front (PPGRF), left ventricular stroke slope (LVSS) and pulse wave velocity.

The systems and methods of the invention utilize physiological data streams from an individual as input in order to a.) assess user continuity i.e., assess whether the same user is continuously wearing and/or operating a device; and b.) monitor physiological state changes i.e. determine whether there are abnormal physiological changes occurring in a user. The data streams can include data exemplified by, but not limited to, heart rate, heart rate variability, blood pressure, breathing rate, cardiopulmonary coupling, actigraphy, accelerometry, circadian rhythms characteristics, and pulse waveform, its derivatives, and associated pulse shape characteristics, such as augmentation index. LVSS, LVET, PPGRF, and pulse wave velocity. In an aspect, user continuity assessment and physiological state change monitoring is done by matching acquired physiological streams to an individual's generated biometric profile. In an aspect, the system and method includes the initial generation of a biometric profile for an individual that can then be compared to later-acquired physiological streams from the individual. In an aspect, the generation of a biometric profile can occur from only one typical sleep session for the user which includes stretches of continuous data streams of the type of data disclosed above about the user. In an aspect, such data streams are collected by wearable data acquisition device.

Moreover, the collection of data streams by the wearable data acquisition device may be relayed between said wearable data acquisition device, a mobile device, and/or a cloud based computing platform, and database for storage of a holistic physiological user profile.

Generated physiological profiles may be used for physiological state change monitoring and/or biometric user continuity assessment in individuals and/or groups of individuals. In particular embodiments, intra-individual differences observed in the patterns of the vital signs are used to construct unique physiological user profiles. Additionally, methods are presented for real time training of said user profiles against which incoming data streams are compared. In particular embodiments, sleep stage, pulse waveform and circadian rhythm-derived input is used to construct unique user profiles, with said profiles subsequently used to monitor abnormal physiological state changes, for the purpose of detecting underlying disease states and/or assessment of user continuity.

In an aspect, the invention is directed to software methods to generate biometric profiles of individuals and/or groups of individuals, from physiological data generated during sleep and related stages, with said method exploits the intra-individual variation manifesting from one or a combination of two or more physiological features, exemplified by, but not limited to: heart rate (HR), RR intervals from which heart rate variability (HRV) is determined, breathing rate (BR), acceleration (ACC) features, arterial pulse wave form together with its derivatives and associated pulse shape characteristics (for example augmentation index), left ventricular stroke slope (LVSS), and pulse wave velocity, blood pressure, cardiopulmonary coupling information, actigraphy, and circadian rhythms-derived features to said biometric profiles. In another aspect, the invention is directed to matching a minimum of one physiological feature obtained from an individual and/or group of individuals to the generated biometric profiles in order to either verify or disprove the identity of the individual/group of individuals from which said biometric profile/s was generated. In another aspect, the invention is directed to methods of applying biometric profiles to identify users and/or groups of users to authenticate a.) activation and deactivation of electronic devices and/or b.) access and usage of electronic devices, said electronic devices exemplified by, but not limited to, wearable, medical, computing, gaming, smart and implantable devices, by matching one of a combination of two or more physiological features to said biometric profiles.

In an aspect, the invention is directed at communicating the created biometric profiles of users and/or groups of users wirelessly from device or platform of origin to remote devices, said devices exemplified by, but not limited to, wearable, medical, computing, gaming, smart and implantable devices and/or cloud-based platforms and databases, exemplified by, but not limited to, medical, insurance and retail databases.

In an aspect, the invention is directed at a device that acquires one or a combination of two or more physiological sleep stage or related data streams, exemplified by, but not limited to: heart rate, heart rate variability, pulse waveform and its derivatives, augmentation index, pulse wave velocity, blood pressure, breathing rate, cardiopulmonary coupling, actigraphy and circadian rhythm characteristics, and communicating said acquired data streams to a cloud-based platform to generate biometric profiles, and communicating said profiles and/or condensed profiles back to said device and/or other device(s), database(s), or cloud-based platform (s), exemplified by, but not limited to medical, insurance or retail databases, wearable, computer, smart and implantable devices.

In an aspect, the invention is directed at a device that acquires one or a combination of two or more physiological sleep stage or related features, exemplified by, but not limited to: heart rate, heart rate variability, pulse waveform and its derivatives, augmentation index, pulse wave velocity, blood pressure, breathing rate, cardiopulmonary coupling, actigraphy and circadian rhythms characteristics, and can generate biometric profiles using said features, and can communicate said biometric profiles to one or a combination of two or more of the following: cloud-based platforms, databases, exemplified by, but not limited to, insurance, medical and retail databases, wearable, computer, smart and implantable devices.

In an aspect, the invention is directed at a method that utilizes intra-individual variations manifesting from physiological features obtained during whole day (24 h) stages with physiological features obtained during sleep and related stages to generate biometric profiles and/or user continuity and physiological state change assessments in individuals and/or groups of individuals.

In an aspect, the invention is directed to software methods generating biometric profiles of individuals and/or groups of individuals from physiological data generated during sleep and related stages, with said methods exploiting the intra-individual variation manifesting from one or a combination of two or more physiological features, and utilizing generated biometric profiles to assess acute and/or chronic physiological state changes in an individual/s, exemplified by, but not limited to: pregnancy, growth, or pathophysiological changes, by matching a minimum of one physiological feature to said profile. In an another aspect, the invention can utilize the biometric profiles for assessing physiological state changes of users and/or groups of users, or condensed versions of said profiles, are communicated wirelessly from device or platform of origin to remote devices, said devices exemplified by, but not limited to, wearable, medical, computing, gaming, smart and implantable devices and/or cloud-based platforms and databases, exemplified by, but not limited to, medical, insurance and retail databases.

In an aspect, the invention is directed to a device that can acquire one or a combination of two or more physiological sleep stage or related features and communicate said acquired features to a cloud-based platform where profiles or condensed profiles are formed, and communicate said profiles and/or condensed profiles back to said device and/or other device(s), database(s), or cloud-based platform(s), exemplified by, but not limited to medical, insurance or retail databases, wearable, computer, smart and implantable devices.

In an aspect, the invention is directed at a device that acquires one or a combination of two or more physiological sleep state or related features, generates biometric profiles using said features, and communicates said biometric profiles to one or a combination of two or more of the following: cloud-based platforms, databases, exemplified by, but not limited to, insurance, medical and retail databases, wearable, computer, smart and implantable devices.

These and other objects and advantages of the invention will become apparent from the following detailed description of the preferred embodiment of the invention.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DETAILED DESCRIPTION AND DRAWINGS

Figure 1:
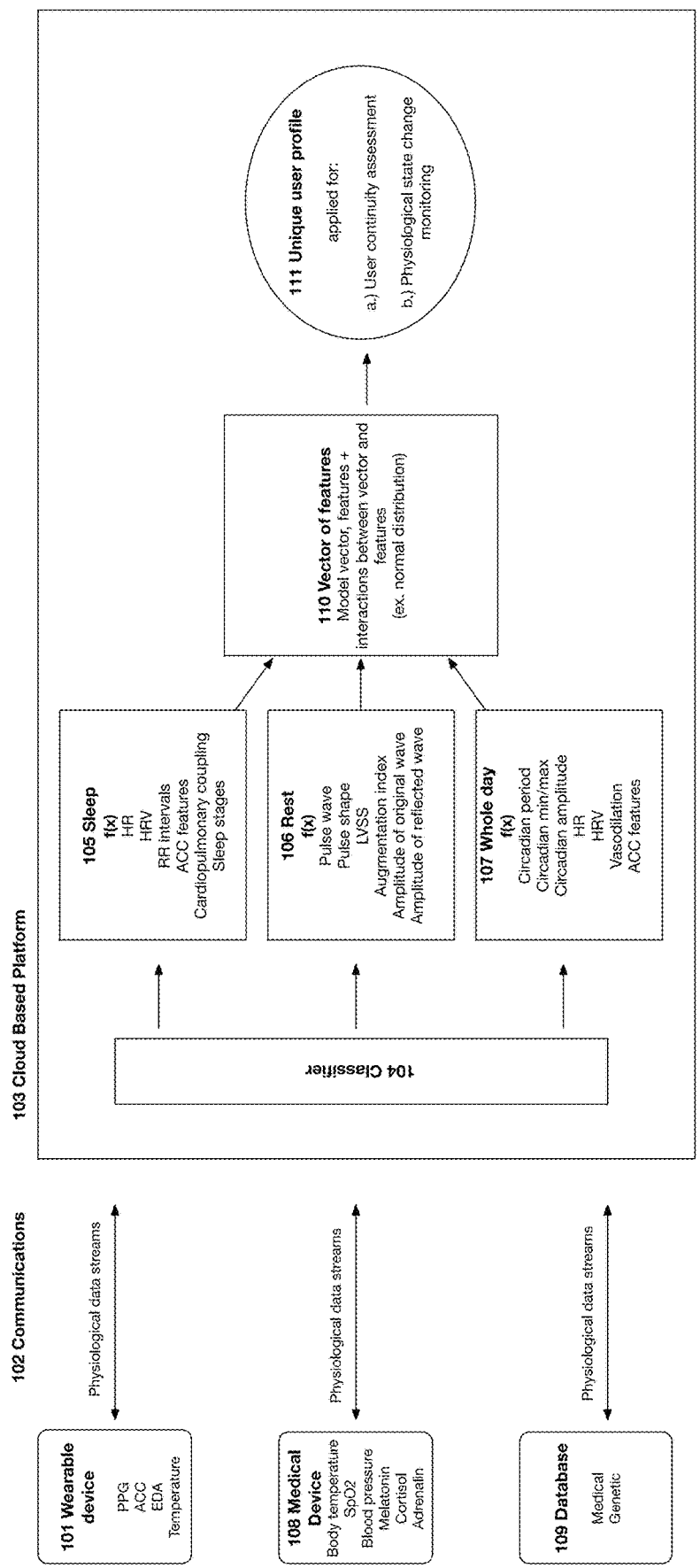
FIG. 1 is a schematic representation of an ecosystem in which preferred embodiments may operate, together with the flow of information with regards to device communication.

FIG. 1 illustrates an aspect of a system and method of the present invention. As shown, the system includes a device 101 associated with a user. In an aspect, the device 101 is a wearable device 101. The device 101 can include, but is not limited to, photoplethysmography (PPG), temperature, electrodermal (EDA) and accelerometer (ACC) sensors. In an aspect, such sensors are used to measure cardiac, motion and temperature signals, exemplified by, but not limited to, heart rate, accelerometry, and body temperature, in order to determine patterns of the vital signs presented during sleep, rest, and free-living stages that are unique to the individual. In an aspect, the wearable device 101 comprises processing means that are configured to take the vital signs (captured as signals) to digitally process them into heart rate and related metrics. In an aspect, the wearable device 101 can include the wearable device disclosed in U.S. patent Ser. No. 14/128,675 entitled "Personalized Nutritional and Wellness Assistant", which is fully incorporated in its entirety herein by reference. In other aspects, the wearable device 101 can be any wearable device 101.

Further biological-based processing may follow, either within the wearable device 101 or sending the heart rate and related metrics over communication networks 102 (e.g., wireless network) to a different device or cloud-based platform 103. In an aspect, on said platform 103, the acquired physiological data streams are segmented into categories. A classifier 104 can segment the data streams into the categories. In an aspect, the classifier 104 can utilize classification algorithm(s), exemplified by, but not limited to, a random forest model, logistic regression, or neural network. In an aspect, the classifier 104 can segment the data streams into biological states. In an exemplary aspect, the biological states include 1. Sleep 105; 2. Rest 106; and 3. Free-living 107.

In an aspect, a list of features is created for each biological state, including, but not limited to: RR intervals from which heart rate variability (HRV) is determined, breathing rate (BR), acceleration (ACC) features, arterial pulse wave form together with its derivatives and associated pulse shape characteristics (for example augmentation index (i.e., systemic arterial stiffness derived from the ascending aortic pressure waveform), LVSS, LVET, PPGRF, and pulse wave velocity), blood pressure, cardiopulmonary coupling information, actigraphy, and circadian rhythm-derived data. In an aspect, $LVET \sim \approx k1/LVSS$ and $LVET \sim = k2/PPGRF$, wherein k1 and k2 are constant. The equation shows that there is an inverse linear relationship between LVET and PPGRF. In an exemplary aspect, when PPGRF is calculated on a pulse with normalized amplitude of 1, k2 would have a value of 1 as well. In other aspects, k2 would be the height of a pulse in the unit wherein it was measured.

Additional input for cloud-based biological processing may also be obtained from other devices, for example, but not limited to, medical devices 108 (e.g. blood pressure devices and pulse oximeters) and databases 109 (e.g., medical and genetic databases which can include information associated to the individual or general information, or both).

A list of features related to the sleep, rest, and free-living states may be extracted from physiological data streams to create a vector (i.e., an n-dimensional representation of an object) of features. This vector of features and the relationship between features may be modeled using any generative modeling technique 110. An example of such a modeling technique is the fitment of a multivariate normal distribution to the vector of features. Observable patterns of the vital signs, resulting from a highly similar physiology, unique to an individual, and yet highly varied between individuals, may be determined from said model. Distributions may be modeled explaining the typical user specific values of each feature, together with the user specific interaction between said features. Such a model forms a unique user profile 111 for a given individual. Simplistic models, such as the above-mentioned fitting of a multivariate normal distribution may be used, together with more complex approaches, such as kernel methods, to capture non-linear relationships. Investigations of non-linear transformations on said features may also be used to capture non-linear relationships. Unique user profiles 111 may subsequently be constructed from said observable patterns.

Constructed user profiles may be used to a) verify whether data obtained from a wearable device is associated with the predetermined owner of the device, regardless of it being exchanged between individuals and b) to determine cues that indicate whether changes have taken place in the physiological state of the user, pointing to occurrences such as, but not limited to: pregnancy, growth, or pathophysiological changes. Subsequently, any such cues may be harnessed to motivate the collecting of additional information, prior to a specific diagnosis.

Methods for Generating Unique User Profiles

In particular embodiments of the claimed invention, physiological data streams obtained by, for example, but not limited to, PPG, ACC, EDA, and temperature sensors contained in a wearable device 101, are communicated wirelessly 102 to a cloud-based platform 103. Additional physiological data streams obtained from databases 109 and other devices 108, such as medical devices 108, may also be communicated to the same platform 103. Acquired physiological data streams are passed through a classifier 104, which can use various classification algorithms, including, but not limited to, a random forest model algorithm, logistic regression algorithm, neural network algorithms, and the like, on said platform 103, with data streams being classified into three biological states, namely 1. Sleep 105 2. Rest 106 3. Free-living 107. Further biological-based processing and modeling 110, to create unique user profiles 111, can follow as described below.

1. Sleep

Biological-based processing (either on the wearable device 101 or on a cloud-based platform 103) results in metrics exemplified by, but not limited to, heart rate (HR), RR interval, heart rate variability (HRV), breathing rate (BR) and acceleration (ACC). On said cloud-based platform, several features, including, but not limited to, HR features, HRV features, ACC features, cardio-pulmonary coupling (CPC) and sleep stage features, are derived by a mapping created from measures such as HR, RR intervals and ACC, to an individual's sleep stages by training machine learning models, such as a bidirectional long short term memory (LSTM) neural network. Typical variation of features and interactions between features may be quantified by the fitting of a multivariate normal distribution. The resulting distribution explains the typical values of each of said features, together with the interaction between said features. Such a model forms a unique profile for a given individual. The above-mentioned fitting of a multivariate normal distribution can be improved by incorporating more complex approaches, such as kernel methods, for the capturing of non-linear relationships and/or investigations of non-linear transformations on features.

Figure 2:
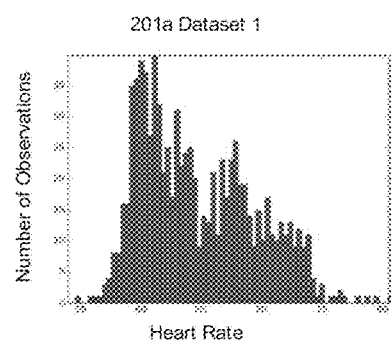
FIG. 2 shows the variability of heart rate distribution during sleep between two different subjects, collected over two nights.
Figure 2:
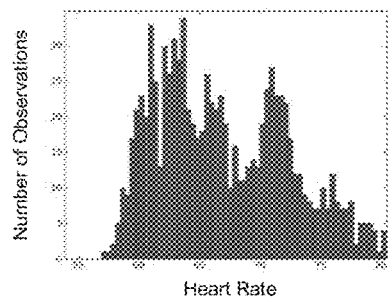
Figure 2:
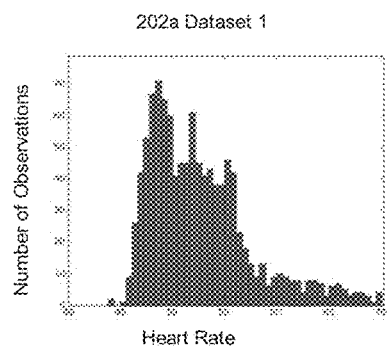
Figure 2:
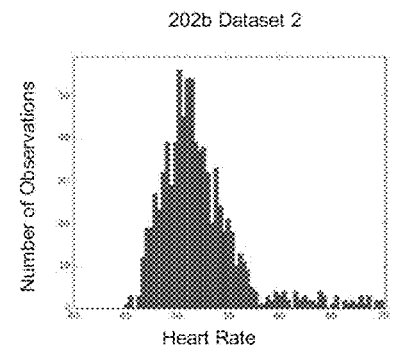

FIG. 2 demonstrates an example of how individual biometric user profiles 111 are generated from sleep stage physiological data streams, exemplified by heart rate during sleep, and may be applied towards identification and/or detection of abnormal physiological conditions. The underlying physiology results in highly similar patterns being generated for an individual each night, but which differs greatly between individuals. This figure demonstrates how individual biometric profiles are generated from physiological data streams, exemplified by heart rate, and its application of identification as well as detection of abnormal physiological conditions.

The variability of heart rate distribution during sleep between two different subjects, collected over two nights, is shown. As observed between subject one 201 and subject two 202, the underlying physiology results in highly similar patterns being generated for an individual each night (201a vs. 201b and 202a vs. 202b), but which differs greatly between individuals (201a and b vs. 202a and b). The heart rate of two individual subjects 201, 202 was measured every second for two nights during sleep (201a, 201b, 202a, 202b), respectively. Thereafter, the range of values is binned (x-axis) and plotted against the number of observations (y-axis) made of a certain heart rate. Similarly, additional features other than heart rate during sleep, together with interactions between said features, may be modeled to contribute to a user specific profile.

2. Rest:

With each heartbeat, a pulse wave propagates through the body's vascular system. The nature of this pulse varies depending on factors such as blood pressure, pulse wave velocity, arterial stiffness and age. These factors vary significantly between individuals, but remain near constant for an individual. In particular embodiments of the invention, these unique pulse waves are detected using photoplethysmogram (PPG) sensors contained in a wearable device 101. In an aspect, the wearable device 101 has internet connectivity capabilities. On-device signal processing results in a typical measured pulse wave form from which features are extracted, exemplified by, but not limited to, the first and second derivatives, augmentation index, LVSS, LVET, PPGRF, amplitude of the original wave, amplitude of the reflected wave and vasodilation. Said extracted features are strongly correlated with factors such as blood pressure, pulse wave velocity, arterial stiffness and age. This renders pulse wave form as an ideal distinguishing factor between individuals. Moreover, when the variation in pulse wave form is compared to heart rate variation, a strong relationship is observed in the sense that varying heart rate exerts a significant yet predictable effect on pulse wave form, and the effect of varying HR on pulse wave can be modeled and compensated for where necessary.

From all above-mentioned features, a multivariate normal distribution, or more complex non-linear methods, such as kernel methods and investigations of non-linear transformations, may be fitted to produce a unique user specific profile.

3. Free-Living

Circadian rhythms are behavioural, physical, and mental changes that adhere to a roughly 24 hour cycle. Through utilizing certain characteristics of several circadian rhythms, such as a) circadian period, b) circadian minimum and maximum values, and c) circadian amplitude, a unique user profile, termed a circadian rhythms profile, can be generated for an individual. As each of these characteristics of circadian rhythms are distinctively different amongst individuals, as well as between physiological processes, multiple circadian rhythm data points may be used to generate user profiles used to identify individuals, or a group of individuals, from a larger group. Said user profiles may also be used to detect underlying physiological state change. For example, the changes can help to determine disease states. Used in combination with sleep and rest stage-generated user profiles, a user may obtain their risk status for clinical disease and/or verification of presence or absence of underlying disease states. An example would be a user with an underlying (and difficult to pick up and diagnose) cardiac electrophysiological disorder. Measured metrics such as RR intervals and heart rate variability may present indications of abnormal cardiac QRS complexes when compared to a normal profile.

In particular embodiments, circadian-rhythm-related physiological data is collected for 24 hours a day at a specific sampling rate with a wearable device 101 and/or medical device 108. The circadian-rhythm-related physiological data can include, but is not limited to, heart rate, skin temperature, core body temperature and heart rate variability. The recorded data may be directly stored on the device 101 for processing and/or uploaded to a cloud-based platform 103 for biological-based processing. On said cloud-based platform 103, several features, including, but not limited to, circadian period, circadian minimum and maximum, circadian amplitude, HR, HRV features, ACC features, and vasodilation features, are derived by a mapping created from measures such as HR, RR intervals and ACC, to an individual's free-living stage by training machine learning models, such as, but not limited to, bidirectional LSTM neural network models. Features derived from circadian rhythm-related data may be considered over a 24-hour period with time-of-day represented on the X-axis and relative change over one cycle represented on the Y-axis. Generated physiological points of intersection that together make up a circadian profile that is unique to an individual.

Typical variation of features and interactions between features (i.e., the quantification of more than one set of features on one plot, how two different sets of features interact) may be quantified by the fitting of a multivariate normal distribution. Such a distribution explains the typical values of each of said features, together with the interaction between said features, forming a unique profile for a given individual. From all above-mentioned features, a multivariate normal distribution, or more complex non-linear methods can be fitted to produce a unique user specific profile. Examples of such models include, but are not limited to, a simplistic model such as fitting of a multivariate normal distribution, and more complex approaches, such as kernel methods for the capturing of non-linear relationships and/or investigations of non-linear transformations on features.

Methods for User Continuity and Physiological State Change Assessments

In order to a.) assess user continuity (i.e., inter-individual comparison to assess whether the same user is continuously wearing and/or operating a device) and b.) monitor physiological state changes (i.e., intra-individual comparison to determine whether there are abnormal physiological changes occurring in a user), incoming physiological data streams may be continuously compared against user profiles generated from data obtained during sleep, rest and free-living states (as described in the previous sections) through real time training of generated user profiles. In particular embodiments, incoming physiological data streams are mapped to a generated user profile by creating a list of features from the data streams associated with sleep, rest and free-living states through real time training of machine learning models such as, but not limited to, bidirectional neural networks. The physiological data streams can include, but are not limited to, RR intervals from which HRV is determined, BR, ACC features, arterial pulse wave form together with its derivatives and associated pulse shape characteristics (for example augmentation index, LVSS, HR derivatives such as entropy calculations, LVET, PPGRF, and pulse wave velocity), blood pressure, cardiopulmonary coupling information, actigraphy, and circadian rhythm-derived data. A vector of features associated with sleep, rest, and free-living states is extracted from physiological data streams. Said vector of features and the relationship between features are modeled using any generative modeling technique, for example, but not limited to, simplistic modeling such as the fitment of a multivariate normal distribution of the vector of features, together with more complex approaches, such as kernel methods to capture non-linear relationships. Investigations of non-linear transformations on said features can be used to capture non-linear relationships. By using the above-mentioned techniques, distributions may be modeled explaining the typical user specific values of each feature, together with user specific interaction between said features. Features from incoming physiological data streams are compared to said distributions using Bayesian modeling techniques to determine, for example, but not limited to, a user specific match and/or abnormal physiological state.

Profiles for Health Measures

In an aspect, intra-divisional differences illustrate the deviations in a biometric profile/fingerprint currently collected to a previously generated (or baseline) biometric profile/fingerprint that is based upon historic data of the identified user. Such deviations can be used to help identify drift in profiles (i.e., change), which can indicate that the user is experiencing a chronic disease state. For example, the HRV high-frequency:low-frequency ratio of a user can form part of his/her biometric fingerprint and will decrease with age. In a person that experiences an increased sympathetic nervous system tone due to a flu infection, this value might decrease much faster and could be used as an alert that the user's physiology is exiting the normal, personalized range of variation.

Profiles for Security Measures

Once an individual's biometric profile has been created, the biometric profile can be used to identify users (inter-individual comparison) for security purposes. In an aspect, various electronic devices are configured to be available to only authorized individuals. Certain biometric profiles can be assigned to the electronic devices. Upon the matching of the biometric profiles, the electronic devices can be activated, deactivated, and/or accessed dependent on the electronic device. In an aspect, the electronic device itself can generate a biometric profile to compare to the stored biometric profile. In other aspects, the electronic device can be in communication with another device that is configured to verify the user. The electronic devices can include, but are not limited to, wearable, medical, computing, gaming, smart and implantable devices.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, those skilled in the art will appreciate that the within disclosures are exemplary only and that various other alternatives, adaptations, and modifications may be made within the scope of the present invention. Accordingly, the present invention is not limited to the specific embodiments as illustrated herein.

What is claimed:

1. A method for biometric identification using physiological data, the method comprising:
   a. receiving at least one physiological data stream of an individual from a device associated with the individual;
   b. deriving at least one physiological metric from the physiological data stream acquired from the device;
   c. exploiting at least one intra-individual variation manifesting from the at least one physiological metric to generate at least one biometric profile for the individual; and
   d. continuously comparing a later acquired physiological data stream from the device to the at least one biometric profile to determine user continuity of the device, wherein continuity is determined from physiological data related to the individual and the later data stream from the device.

2. The method of claim 1, wherein the at least one physiological metric includes heart rate, heart rate variability, blood pressure, breathing rate, cardiopulmonary coupling, actigraphy, accelerometry, circadian rhythms characteristics, or a pulse waveform.

3. The method of claim 2, wherein the at least one physiological metric comprises the pulse waveform and wherein the pulse waveform includes pulse waveform derivatives or associated pulse shape characteristics.

4. The method of claim 3, wherein the associated pulse shape characteristics includes an augmentation index, a left ventricular stroke slope (LVSS), a left ventricular ejection time (LVET), a photoplethysmographic rising front (PPGRF), or a pulse wave velocity.

5. The method of claim 1, wherein the comparing the later acquired physiological data stream from the device to the at least one biometric profile further comprises monitoring physiological state changes of the individual.

6. The method of claim 5, wherein the monitoring of physiological state changes of the individual is utilized to detect underlying disease states.

7. The method of claim 1, wherein acquiring the at least one physiological data stream further comprises classifying the at least one physiological data stream into one or more biological states.

8. The method of claim 7, wherein the one or more biological state is classified as sleep, rest, or free living, wherein free living is a biological state that is not sleep or rest.

9. The method of claim 8, wherein the biological state is sleep, the at least one biometric profile is derived by a mapping created from at least one physiological data stream by a training machine learning model.

10. The method of claim 9, wherein the machine learning model comprises a bidirectional long short term memory (LSTM) neural network.

11. The method of claim 1, wherein the physiological data stream is collected using a wearable data acquisition device.

12. The method of claim 11, wherein a portion of the physiological data stream is relayed from the wearable data acquisition device to a mobile device, a cloud based computing platform, or a database.

13. The method of claim 1, wherein the at least one biometric profile is trained in real-time against an incoming physiological data stream.

14. The method of claim 1, wherein the at least one biometric profile comprises a baseline biometric profile, wherein the method continuously performs steps a-c for the later acquired physiological data streams to create additional biometric profiles, and further comprising comparing the additional biometric profiles to the baseline biometric profile to monitor drift in the plurality of biometric profiles.

15. A system for biometric identification using physiological data, the system comprising:
an electronic device comprising:
processing means;
communication means in communication with the processing means; and
a database in communication with the processing means and the communication means, wherein the processor is configured to:
receive at least one physiological data stream of an individual from a device associated with the individual;
derive at least one physiological metric from the physiological data stream acquired from the device;
exploit at least one intra-individual variation manifesting from the at least one physiological metric to generate at least one biometric profile for the individual;
store the at least one biometric profile in the database; and
continuously compare the at least one biometric profile to another physiological metric from the device to determine user continuity of the device, wherein continuity is determined from physiological data related to the individual and the another physiological metric from the device.

16. The system of claim 15, wherein the at least one physiological metric comprises heart rate, heart rate variability, blood pressure, breathing rate, cardiopulmonary coupling, actigraphy, accelerometry, circadian rhythms characteristics, or pulse waveform.

17. The system of claim 16, wherein the at least one physiological metric is the pulse waveform, and wherein the pulse waveform comprises associated pulse shape characteristics, wherein the associated pulse shape characteristics comprises an augmentation index, a left ventricular stroke slope (LVSS), a left ventricular ejection time (LVET), a photoplethysmographic rising front (PPGRF), or a pulse wave velocity.

18. The system of claim 15, wherein the at least one stored biometric profile is compared to another physiological metric in order to verify or disprove the identity of the at least one individual.

19. The system of claim 18, wherein upon verification the electronic device is activated and upon disproval the electronic device is deactivated.

20. The system of claim 19, wherein the electronic device further comprises sensors to capture the at least on physiological data stream.

21. The system of claim 20, wherein the physiological data stream is acquired with the electronic device and communicated to at least one cloud-based platform to generate the at least one biometric profile, wherein upon generation at least a portion of the at least one biometric profile is communicated back to the electronic device.

22. The system of claim 15, wherein the at least one physiological data stream is obtained for at least one twenty-four (24) hour period.

23. The system of claim 22, wherein the at least one biometric profile is utilized to assess acute and chronic physiological state changes by matching the at least one physiological metric to at least one biometric profile stored in the database.

24. The system of claim 23, wherein the acute and chronic physiological state changes comprise one or more of pregnancy, growth and pathophysiological changes.

25. The system of claim 24, wherein the at least one cloud-based platform segments the physiological data stream into categories using a classifier.

26. The system of claim 25, wherein the classifier utilizes one or more of the following classification algorithms to segment the physiological data stream: a random forest model, a logistic regression algorithm, and a neural network algorithm.

27. The system of claim 25, wherein the at least one cloud-based platform segments the physiological data stream into one or more biological states.

28. The system of claim 27, wherein the one or more biological state is classified as sleep, rest or free-living, wherein free living is a biological state that is not sleep or rest.

29. The system of claim 28, wherein at least one feature related to the biological states is extracted from the physiological data stream to create a vector of features modeled using a generative modeling technique to generate the at least one biometric profile.

* * * * *